United States Patent [19]

Mader

[11] 4,078,181
[45] Mar. 7, 1978

[54] RADIATION APPARATUS WITH REFLECTOR CASING

[75] Inventor: Helmut Mader, Bovenden, Germany

[73] Assignee: Dr. Kern GmbH, Gottingen, Germany

[21] Appl. No.: 641,491

[22] Filed: Dec. 17, 1975

[30] Foreign Application Priority Data

Feb. 12, 1975 Germany .................. 7504185[U]

[51] Int. Cl.² .............................................. G01J 1/00
[52] U.S. Cl. ...................................... 250/495; 250/504
[58] Field of Search ........................ 250/494, 495, 504

[56] References Cited

U.S. PATENT DOCUMENTS

| 2,072,205 | 3/1937 | Halpern | 250/495 |
| 2,198,770 | 4/1940 | Goodrich | 250/495 |
| 2,551,319 | 5/1951 | Eiklid | 250/495 |

Primary Examiner—Bruce C. Anderson

[57] ABSTRACT

A radiation apparatus includes a reflector which is separated from and projects out of the adjacent supporting surfaces. The reflector is connected to the adjacent surfaces by a plurality of spaced-apart bridges.

1 Claim, 3 Drawing Figures

U.S. Patent  March 7, 1978  4,078,181
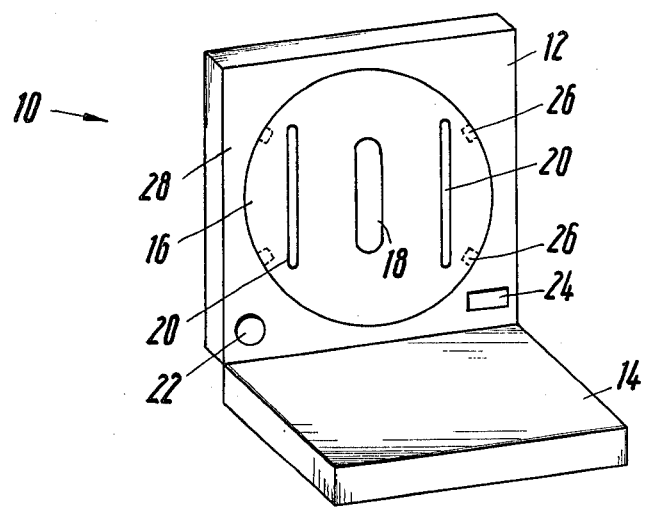
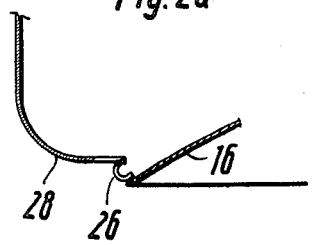
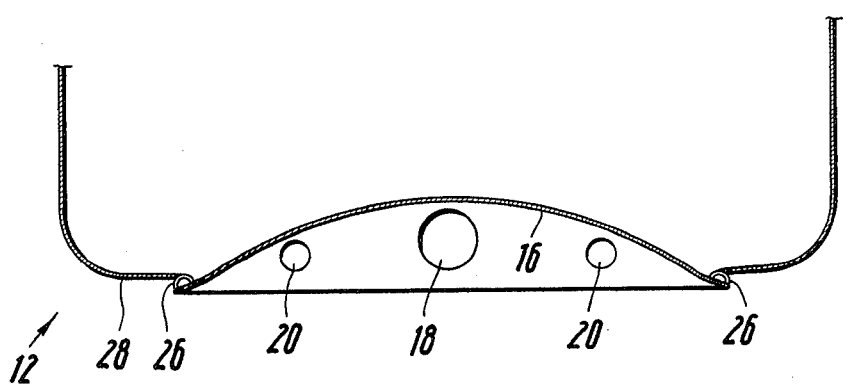

4,078,181

RADIATION APPARATUS WITH REFLECTOR CASING

BACKGROUND AND SUMMARY OF THE INVENTION

This innovation refers to a radiation apparatus for cosmetic and/or medical purposes with ultraviolet and infrared radiation sources mounted in a reflector.

Radiation apparatus of conventional construction in most cases have, aside from the reflector proper, i.e., the active part, adjacent surfaces carrying the operating equipment and furnishing space between the casing. Experience has shown that the parts adjacent to the active reflector will become very hot. This undesired heating is caused by conduction of heat. The upper surfaces are additionally heated by the ascending hot air. For the most part the surfaces surrounding the reflector are made of a metallic piece of material out of which the reflector is formed (German Specification 1,764,399). The cavity of the reflector then merges into the surrounding surfaces, and these metallic parts become very hot during operation.

It is the object of this innovation to remove the aforementioned disadvantages but nevertheless to provide a radiation apparatus of simple construction.

This problem is solved in that reflector is separated from, set off against, and projecting from the adjacent surfaces of radiation apparatus.

The reflector and the adjacent surfaces are stamped out of one piece and are thereafter separated by means of an appropriate cutting tool. A connection can be made between these parts by bridges of a suitable material. The air space existing between the reflector and the walls reduces the conduction of heat between these parts and prevents excessive heating. Heating of the upper surfaces is further prevented by letting the reflector protrude from the adjacent walls so that the ascending air does not sweep along these surfaces. It was found that adjacent surfaces have a temperature of about 25° less than that of the reflector.

DESCRIPTION OF THE DRAWING

Further details, features and advantages of the innovation will be apparent upon consideration of the following description of the drawing, wherein:

FIG. 1 is a schematic perspective view of a radiation apparatus;

FIG. 2 is the elevation of a reflector with upper part of the radiation apparatus; and FIG. 2a shows a connection between reflector and adjacent surfaces of the radiation apparatus.

DESCRIPTION OF SPECIFIC EMBODIMENT

In FIG. 1 a radiation apparatus 10 is schematically shown, consisting of an upper part 12 and a lower part 14, which are joined to each other by means of a hinge. The upper part 12 embodies a reflector 16, in which are arranged an ultraviolet radiation source 18 and infrared radiation sources 20, and operating elements 22 and 24, i.e., a microchronometer or an automatic switch 22 and a switch 24, by which the infrared radiation sources 20 can be operated separately from the ultraviolet radiation source 18.

It can be seen from FIG. 2 that the reflector 16 and the adjacent surfaces 28 of the upper part 12 are separated from each other and kept in distance to each other. They are joined only by narrow connecting bridges. In the embodiment illustrated, there are four connecting bridges, which are arranged in the relatively cooler portions of the reflector. The separated connections form an air gap between the active reflector 16 and the adjacent surfaces 28 so that only an insignificant conduction of heat takes place between these parts.

From FIG. 2 it is likewise apparent that the reflector 16 is standing out from the adjacent surfaces 28. This distance, amounting to 3 to 5 mm in the illustrated embodiment, ensures that the ascending hot air does not sweep along the upper external surfaces, so that in this case, too, an undesired heating is prevented, FIG. 2a shows a possible configuration of the connecting bridge 26 between the reflector 16 and the adjacent surfaces 28.

The connecting bridges 26 simultaneously offer the advantage that during the preliminary mounting of the reflector, mechanical and electrical connections between the operating areas 22, 24 and the active reflector 16 can be easily made. Notwithstanding the separation between the reflector 16 and the surfaces 28, the connecting bridges 26 allow a simultaneous galvanic processing of the unit made up of the reflector 16 and the surfaces 28.

While in the foregoing specification a detailed description of a specific embodiment of the invention was set forth for the purpose of illustration, it is to be understood that many of the details hereingiven may be varied considerably by those skilled in the art without departing from the spirit and scope of the invention.

I claim:

1. A radiation apparatus having a dome-shaped reflector and a supporting surface adjacent the reflector for supporting the reflector and extending radially outwardly from the reflector and ultraviolet and infrared radiation sources positioned in the reflector, the improvement characterized by the reflector being connected to the supporting surface and supported by a plurality of spaced-apart bridges which extend from adjacent the outer periphery of the reflector to the supporting surface to prevent substantial heat conduction between said reflector and said supporting surface, the reflector and the supporting surface being stamped integrally from a single piece of metal, and the reflector and the supporting surface being separated from each other by an air gap except at the bridges, the reflector having a front edge projecting outwardly beyond the supporting surface whereby hot air rising from the reflector is spaced from the supporting surface.

* * * * *